(12) United States Patent
Leith et al.

(10) Patent No.: US 12,053,164 B2
(45) Date of Patent: Aug. 6, 2024

(54) RESPIRABLE AND THORACIC SAMPLING INLET ASSEMBLIES

(71) Applicants: Access Sensor Technologies LLC, Fort Collins, CO (US); Colorado State University Research Foundation, Fort Collins, CO (US)

(72) Inventors: David Leith, Chapel Hill, NC (US); John Volckens, Fort Collins, CO (US); Christian L'Orange, Fort Collins, CO (US); Daniel D. Miller-Lionberg, Denver, CO (US)

(73) Assignees: Colorado State University Research Foundation, Fort Collins, CO (US); Access Sensor Technologies LLC, Fort Collins, CO (US)

( * ) Notice: Subject to any disclaimer, the term of this patent is extended or adjusted under 35 U.S.C. 154(b) by 748 days.

(21) Appl. No.: 17/127,520

(22) Filed: Dec. 18, 2020

(65) Prior Publication Data
US 2021/0196244 A1  Jul. 1, 2021

Related U.S. Application Data

(60) Provisional application No. 62/951,990, filed on Dec. 20, 2019.

(51) Int. Cl.
*A61B 10/00* (2006.01)
*G01N 1/22* (2006.01)
*G01N 15/02* (2024.01)

(52) U.S. Cl.
CPC ........... *A61B 10/00* (2013.01); *G01N 1/2208* (2013.01); *G01N 1/2211* (2013.01);
(Continued)

(58) Field of Classification Search
CPC ....... G01N 1/2208; G01N 1/2211; A61B 5/08
See application file for complete search history.

(56) References Cited

U.S. PATENT DOCUMENTS

| | | |
|---|---|---|
| 4,301,002 A | 11/1981 | Loo |
| 4,827,779 A | 5/1989 | Marple et al. |
| (Continued) | | |

FOREIGN PATENT DOCUMENTS

WO    2019/226955 A1    11/2019

OTHER PUBLICATIONS

International Preliminary Report on Patentability received for PCT Patent Application No. PCT/US2020/066145, mailed on Jun. 30, 2022, 11 pages.
(Continued)

*Primary Examiner* — Puya Agahi
(74) *Attorney, Agent, or Firm* — Faegre Drinker Biddle & Reath LLP

(57) ABSTRACT

A portable sampler, the sampler including a sampler assembly having a housing that includes a receiver defined therein for interchangeably receiving a number of removable inlet assemblies, the removable inlet assemblies including a respirable inlet assembly and a thoracic inlet assembly. The respirable inlet assembly includes a hybrid cyclone assembly, the hybrid cyclone assembly including an impaction stage and a cyclone in series. The thoracic inlet assembly includes an inlet slot configured to function as a size-selective inlet. Another thoracic inlet assembly includes a housing having a number of openings configured to receive a sample airflow; an inlet insert through which an inlet aperture is defined; a prequalification chamber defined between a lower surface of the housing and an upper surface of the inlet insert; and a protrusion extending downward
(Continued)

from the lower surface of the housing into the inlet aperture of the inlet insert to from an inlet slot.

13 Claims, 12 Drawing Sheets

(52) U.S. Cl.
CPC ....... G01N 1/2273 (2013.01); G01N 15/0255 (2013.01); *A61B 2010/0087* (2013.01); *G01N 2015/0261* (2013.01)

(56) References Cited

U.S. PATENT DOCUMENTS

| | | | |
|---|---|---|---|
| 4,941,899 A | | 7/1990 | Liu |
| 6,688,187 B1 * | | 2/2004 | Masquelier .......... G01N 1/2214 |
| | | | 73/863.22 |
| 8,689,648 B1 | | 4/2014 | Heff |
| 2011/0203931 A1 | | 8/2011 | Novosselov et al. |
| 2017/0370809 A1 * | | 12/2017 | Miller-Lionberg .......................... |
| | | | G01N 1/2202 |

OTHER PUBLICATIONS

International Search Report and Written Opinion received for PCT Patent Application No. PCT/US2020/066145, mailed on Jun. 10, 2021, 19 pages.

* cited by examiner

RESPIRABLE AND THORACIC SAMPLING INLET ASSEMBLIES

CROSS-REFERENCE TO RELATED APPLICATION

This application claims priority to U.S. Provisional Application No. 62/951,990, titled "Respirable and Thoracic Sampling Inlet Assemblies," filed on Dec. 20, 2019, the entire disclosure of which is hereby incorporated by reference in its entirety.

STATEMENT REGARDING FEDERALLY SPONSORED RESEARCH OR DEVELOPMENT

This invention was made with government support under R01 OH010662 awarded by the National Institutes of Health. The government has certain rights in the invention.

FIELD

Embodiments of the disclosed subject matter include wearable air sampling devices. More specifically, embodiments include sampling devices having respirable and/or thoracic sampling inlet assemblies.

BACKGROUND

Respirable and thoracic mass sampling have been used for many years to assess personal exposure to particulate pollutants that deposit in the alveolar and thoracic regions of the lung. Both methods fractionate particles by aerodynamic size, so that sampled aerosol is more representative of what penetrates to the relevant regions of the respiratory tract (i.e., to mimic aerosol intake). Standards have been set that describe the relationship between aerodynamic particle diameter and sampler collection efficiency for both respirable and thoracic mass sampling, and an important design objective is to match a sampler's performance with its standard.

SUMMARY

A portable sampler, the sampler including a sampler assembly having a housing that includes a receiver defined therein for interchangeably receiving a number of removable inlet assemblies, the removable inlet assemblies including a respirable inlet assembly and a thoracic inlet assembly. The respirable inlet assembly includes an upper housing and a lower housing, a number of primary inlet apertures disposed in the upper housing configured to receive a sample airflow, and a hybrid cyclone assembly including an impaction stage and a cyclone stage in series. The thoracic inlet assembly includes a housing with an upper surface, an inlet aperture defined through the upper surface, and an inlet slot configured to function as a size-selective inlet for the inlet aperture.

Another thoracic inlet assembly includes a housing having an upper surface and a lower surface, the housing having a number of openings configured to receive a sample airflow; an inlet insert through which an inlet aperture is defined; a prequalification chamber defined between the lower surface of the housing and an upper surface of the inlet insert; and a protrusion extending downward from the lower surface of the housing into the inlet aperture of the inlet insert to from an inlet slot. In an example, the inlet aperture includes a size-selective outlet through which the sample airflow from the inlet slot passes. As another example, the thoracic inlet assembly further includes a filter cartridge comprising a sampling chamber defined by an upper surface of a filter cartridge base and a lower surface of a filter cartridge cap, the size-selective outlet opening into the sampling chamber, and the sampling chamber configured to receive a sampling filter.

While multiple embodiments are disclosed, still other embodiments of the subject matter will become apparent to those skilled in the art from the following detailed description, which shows and describes illustrative embodiments of the subject matter. Accordingly, the drawings and detailed description are to be regarded as illustrative in nature and not restrictive.

Figure 1:
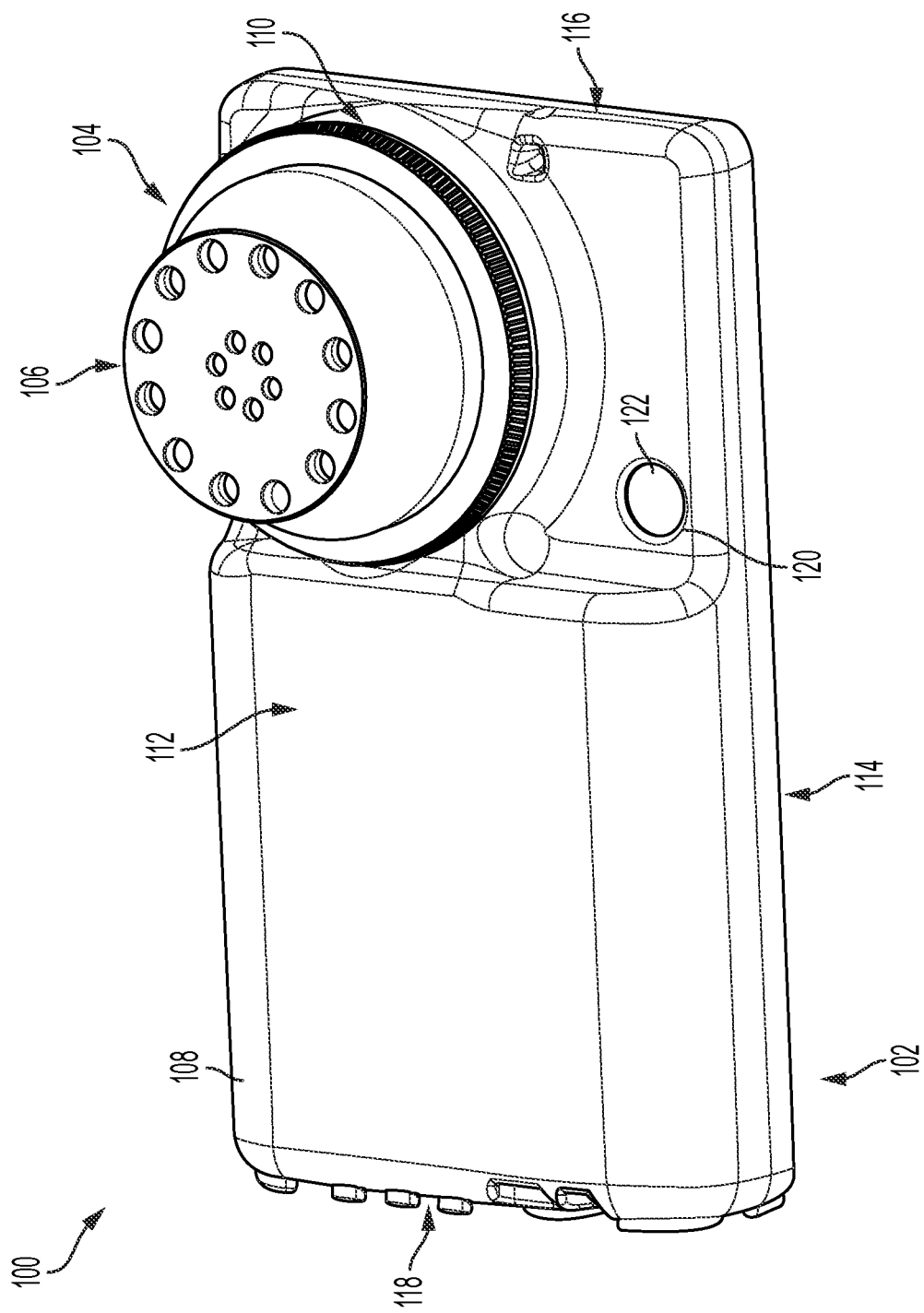
FIG. 1 depicts an illustrative personal air sampler, in accordance with embodiments of the subject matter disclosed herein.

While embodiments of the disclosed subject matter are amenable to various modifications and alternative forms, specific embodiments have been shown by way of example in the drawings and are described in detail below. The intention, however, is not to limit the subject matter to the particular embodiments described. On the contrary, the subject matter is intended to cover all modifications, equivalents, and alternatives falling within the ambit of the disclosure as defined by the appended claims.

Moreover, although the term "block" may be used herein to connote different elements of methods or algorithms employed, the term should not be interpreted as implying any particular order among or between various steps herein disclosed unless and except when the order of individual steps is explicitly described The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

DETAILED DESCRIPTION

Embodiments of the two-stage inlet assembly described herein for respirable mass sampling utilizes an impaction stage and a cyclone, whereas the one-stage inlet for thoracic mass sampling utilizes a circular slot impactor. Inlet designs are based on particle collection theory used in conjunction with an optimization algorithm to predict initial inlet dimensions; and these predictions were the starting points for experiments that finalized dimensions and operating conditions. Both the respirable mass inlet and the thoracic mass inlet described here may be interchangeably coupled to a sampler such as, for example, the portable air sampling device described in U.S. application Ser. No. 15/442,657, filed Feb. 25, 2017, the entirety of which is incorporated by reference herein for all purposes.

FIG. 1 depicts an illustrative portable air sampler 100. In embodiments, the sampler 100 can be worn or carried by a user to facilitate collection of particles from the user's environment such as, for example, in a region corresponding to air that the user breathes. The sampler 100 includes a sampler assembly 102 and a removable inlet assembly 104. In embodiments, the inlet assembly 104 may include a size-selective inlet 106 configured to select a certain size of particles to be sampled. In embodiments, the inlet assembly 104 may include a removable substrate (not shown) upon which particles may be deposited. According to embodiments, the substrate can be a transmission electron microscopy grid, a thin foil substrate, any number of other types of substrates, and/or the like. According to embodiments, the sampler 100 may be, be similar to, include, or be included in any number of different types of portable air samplers. For example, in embodiments, the sampler 100 may include a portable air sampling device, as described, for example, in U.S. patent application Ser. No. 15/442,657, filed Feb. 25, 2017 and claiming priority to U.S. Provisional Patent Application No. 62/354,019, filed on Jun. 23, 2016, each of which is hereby expressly incorporated by reference in its entirety for all purposes. In embodiments, the sampler 100 may be any number of different types of samplers.

As shown in FIG. 1, embodiments of the sampler 100 includes a housing 108 having a receiver 110 defined in a first side 112, a second side 114 opposite the first side 112, a first end 116, and a second end 118. According to embodiments, the receiver 110 may be configured to receive any number of different, interchangeable, inlet assemblies. That is, for example, the sampler 100 may be used to collect airborne particulate matter of two or more different sizes based on the inlet assembly that is coupled to the receiver 110. For example, in embodiments, the sampler 100 may be configured to perform respirable mass sampling when a respirable inlet assembly is coupled to the receiver 110, thoracic mass sampling when a thoracic inlet assembly is coupled to the receiver 110, and/or the like. As shown in FIG. 1, the housing 108 may have a generally rectangular shape, although in embodiments, any number of other configurations can be used for the housing 108. In embodiments, the housing 108 can include a clip (not shown) that is coupled thereto and that can be used to clip the sampler 100 to an article of clothing. In embodiments, the housing 108 can include other mechanisms for facilitating wearing of the sampler 100 by a user such as, for example, a strap, a hook-and-loop system (e.g., Velcro®), and/or the like.

In embodiments, the housing 108 can include any number of input devices and/or output devices such as, for example, buttons, a touch-screen, switches, roller, slider, and/or the like. In the illustrated embodiment, for example, the first side 112 of the housing 108 includes an aperture 120 through which an indicator 122 can be viewed. In embodiments, the indicator 122 can be, for example, an LCD screen, an LED screen, one or more LED lights, a touch-screen, and/or the like. In embodiments, for example, the indicator 122 can be used to indicate whether the sampler 100 is powered on or off, whether the sampler 100 is actively sampling air, and/or the like.

The illustrative sampler 100 shown in FIG. 1 is not intended to suggest any limitation as to the scope of use or functionality of embodiments of the subject matter disclosed throughout this document. The illustrative sampler 100 also should not be interpreted as having any dependency or requirement related to any single component or combination of components illustrated therein. For example, in embodiments, the illustrative sampler 100 can include additional components. Additionally, any one or more of the components depicted in FIG. 1 can be, in embodiments, integrated with various ones of the other components depicted therein (and/or components not illustrated). Any number of other components or combinations of components can be integrated with the illustrative sampler 100 depicted in FIG. 1, all of which are considered to be within the ambit of this disclosure.

Respirable Mass Inlet

Figure 2A:
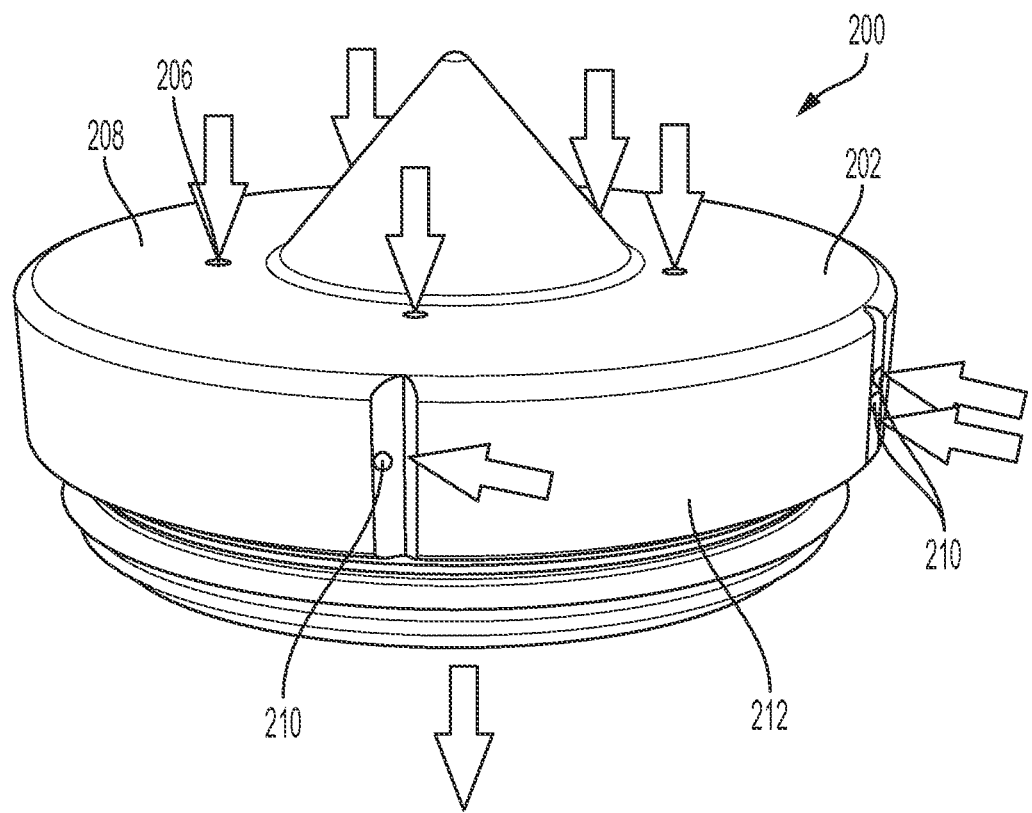
FIG. 2A is a schematic perspective view of a portion of an illustrative respirable inlet assembly, in accordance with embodiments of the subject matter disclosed herein.
Figure 2B:
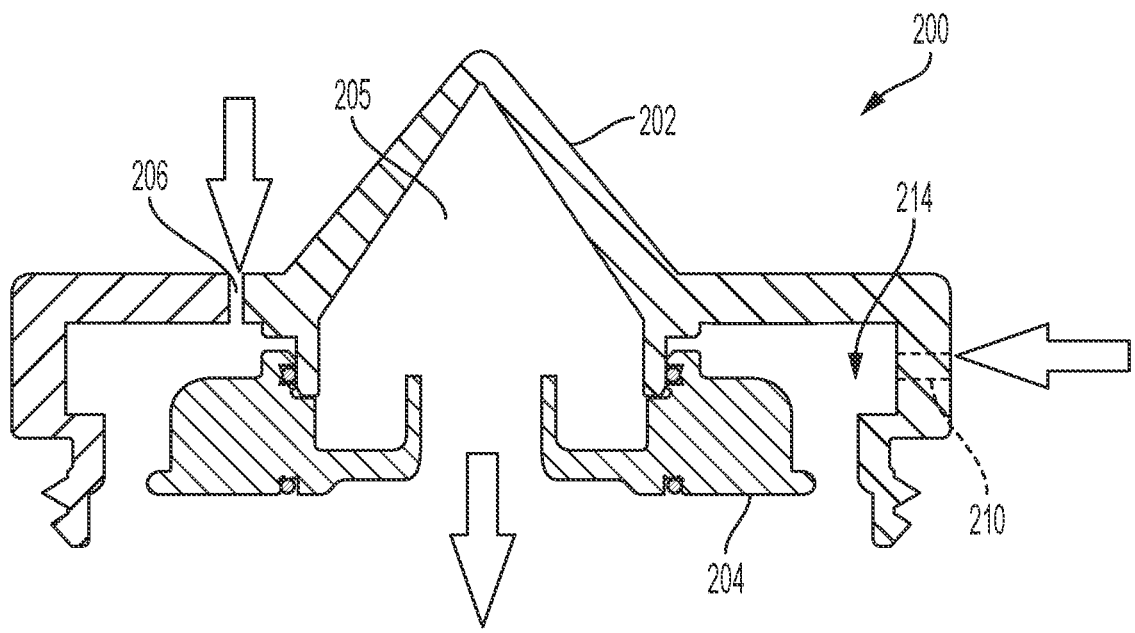
FIG. 2B is a cross-sectional schematic side view of the portion of the illustrative respirable inlet assembly depicted in FIG. 2A, in accordance with embodiments of the subject matter disclosed herein.

FIG. 2A is a schematic perspective view of a portion of an illustrative respirable inlet assembly 200, in accordance with embodiments of the subject matter disclosed herein; and FIG. 2B is a cross-sectional schematic side view of the portion of the illustrative respirable inlet assembly 200 depicted in FIG. 2A, in accordance with embodiments of the subject matter disclosed herein. According to embodiments, the respirable inlet assembly 200 may be configured to be received by a receiver of a sampler (e.g., the receiver 110 of the sampler 100 depicted in FIG. 1) to configure the sampler for respirable mass sampling.

As shown in FIGS. 2A and 2B, the portion of the respirable inlet assembly 200, which may be referred to herein as a hybrid cyclone assembly, includes an upper housing portion 202 configured to be coupled to a lower housing portion 204 to form a cyclone cavity 205 therein. The standard for respirable mass sampling specifies that sampler collection efficiency should gradually increase with particle diameter, reach a value of 0.5 at 4 µm, and unity at about 10 µm. The respirable mass inlet assembly 200 utilizes an impaction stage and a cyclone in series, arranged so that only part of the sample flow passes through the impaction stage (e.g., via impactor inlet apertures 206) but all of the sample flow passes through the cyclone (e.g., from both impactor inlet apertures 206 and impactor bypass apertures 210). The impaction stage flattens the slope of the performance curve by collecting small particles that the cyclone misses. Allowing some incoming flow to bypass the impaction stage keeps the sampler from collecting too many large particles.

As shown, the upper housing portion 202 includes one or more impactor inlet apertures 206 disposed in an upper surface 208 of the upper housing portion 202. Additionally, as shown in FIG. 2A, a number of impactor bypass apertures 210 are disposed in a side surface 212. As shown, some sample air enters the impaction stage through impactor inlet apertures 206. From the impaction stage, this air enters a toroidal plenum 214, as shown in FIG. 2B. Other sample air bypasses the impaction stage and enters the plenum 214 through the impactor bypass apertures 210. It will be appreciated that "bypassing" the impaction stage may refer to such instances where the effect of the impaction stage is reduced. For example, sample air entering through impactor bypass apertures 210 may travel about 30 jet diameters before they reach a plenum surface, thereby reducing or otherwise minimizing impaction as compared to sample flow entering through impact inlet apertures 206. The combined sample flow leaves the plenum 214 by way of a tangential cyclone inlet (not shown in the figure), then goes through the cyclone 205 and out to a filter (not shown).

In embodiments, all of the inlet apertures may have the same, or similar, diameter and length so that flow through each will be approximately equal. The inlet assembly 200 may include any number of impactor inlet apertures and/or bypass inlet apertures. In an embodiment, for example, the inlet assembly may include eight impactor inlet aperture and four impactor bypass apertures. The proportion of sampled air that flows through the impaction stage may be approximated by the number of impactor inlet apertures divided by the total number of impactor and bypass apertures. According to embodiments, the diameter of each aperture may be any number of different sizes. In embodiments, the diameter may be, for example, approximately 1.0 mm. A diameter of approximately 1.0 mm may provide practical benefits. For example, smaller apertures may be more difficult to keep clean, whereas larger apertures may reduce impactor efficiency and could allow coarse grit to enter the sampler.

The illustrative respirable inlet assembly 200 shown in FIGS. 2A and 2B is not intended to suggest any limitation as to the scope of use or functionality of embodiments of the subject matter disclosed throughout this document. The illustrative respirable inlet assembly 200 also should not be interpreted as having any dependency or requirement related to any single component or combination of components illustrated therein. For example, in embodiments, the illustrative respirable inlet assembly 200 can include additional components. Additionally, any one or more of the components depicted in FIGS. 2A and 2B can be, in embodiments, integrated with various ones of the other components depicted therein (and/or components not illustrated). Any number of other components or combinations of components can be integrated with the illustrative respirable inlet assembly 300 depicted in FIGS. 2A and 2B, all of which are considered to be within the ambit of this disclosure.

Figure 3A:
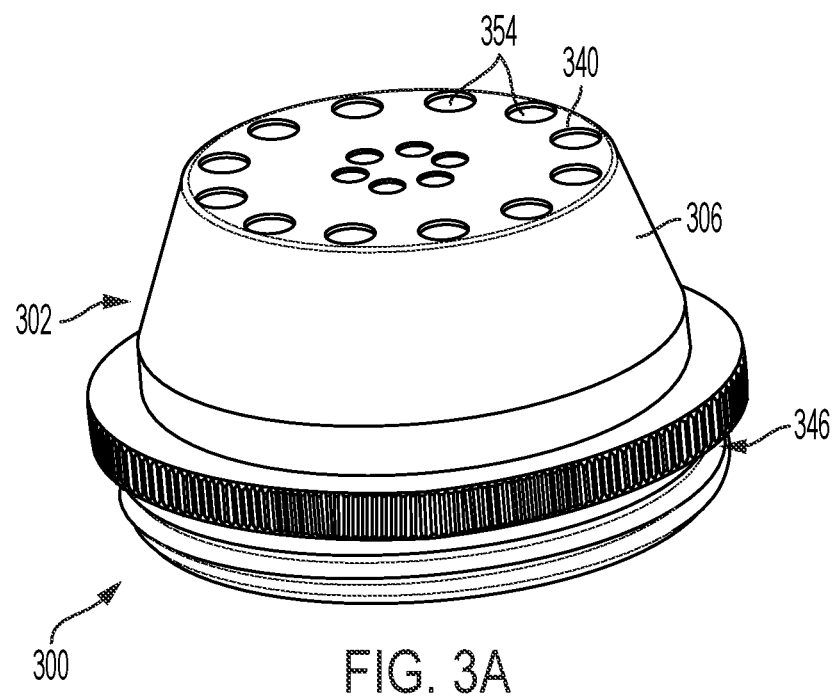
FIG. 3A is a perspective view of an illustrative respirable inlet assembly, in accordance with embodiments of the subject matter disclosed herein.
Figure 3B:
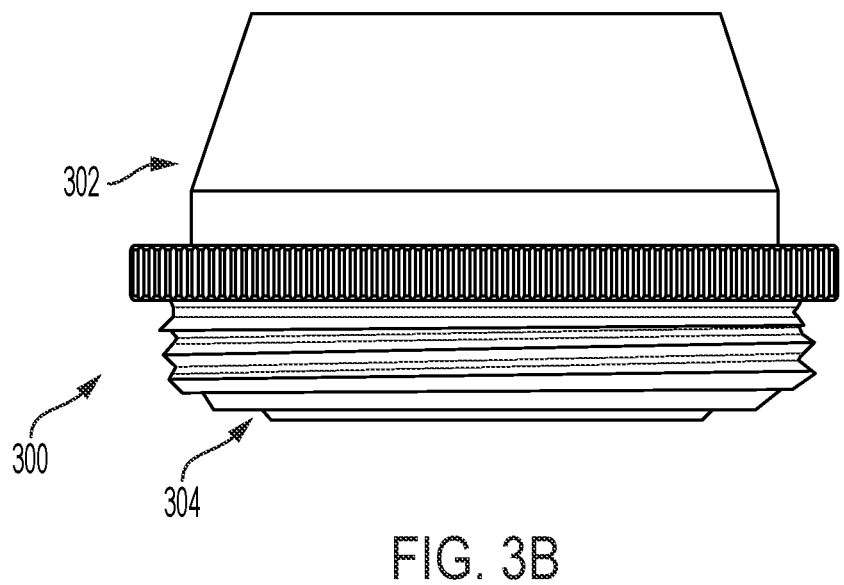
FIG. 3B is a side view of the illustrative respirable inlet assembly depicted in FIG. 3A, in accordance with embodiments of the subject matter disclosed herein.
Figure 3C:
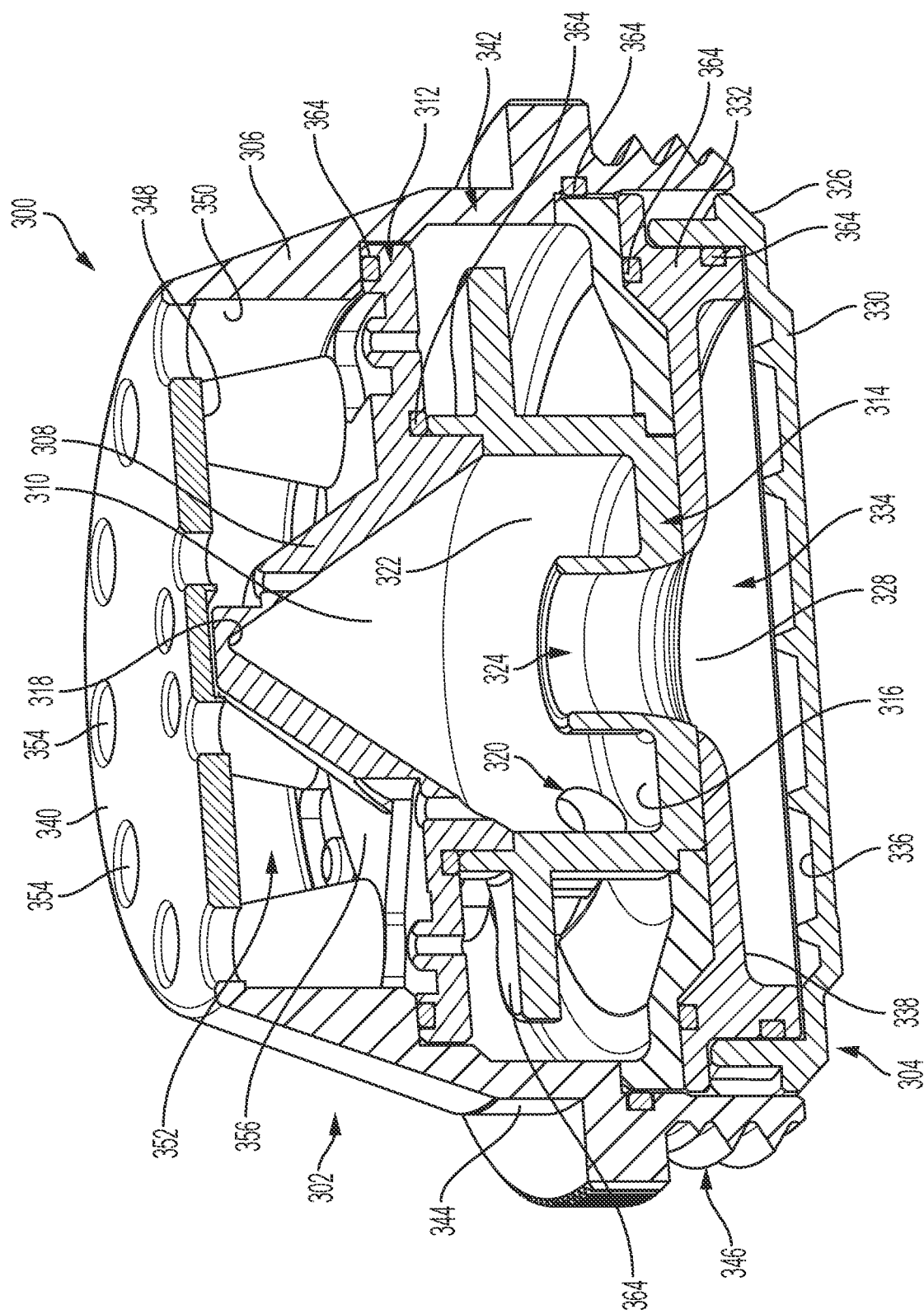
FIGS. 3C and 3D are cross-sectional perspective views of the illustrative respirable inlet assembly depicted in FIGS. 3A and 3B, in accordance with embodiments of the subject matter disclosed herein.
Figure 3D:
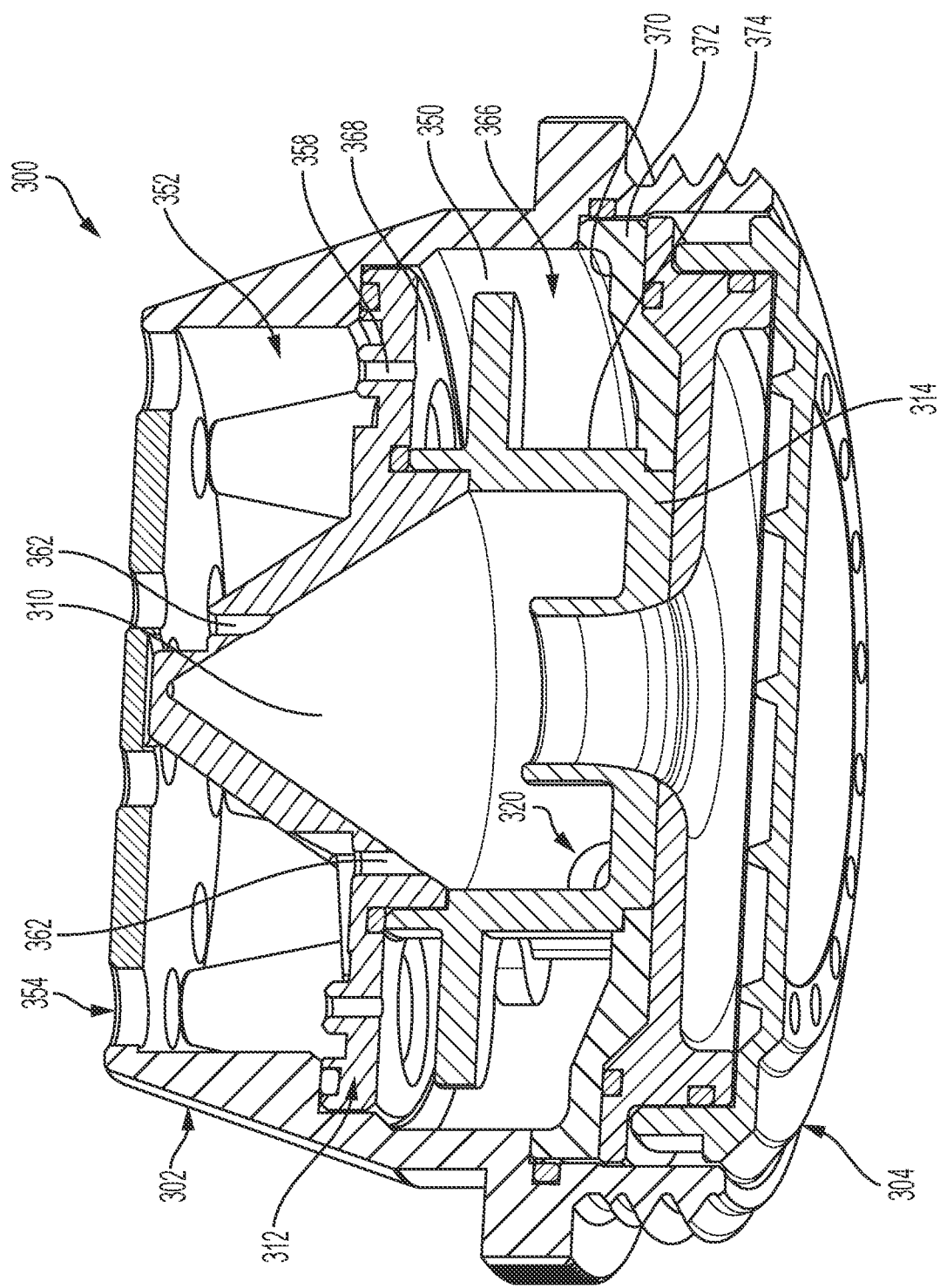
Figure 3E:
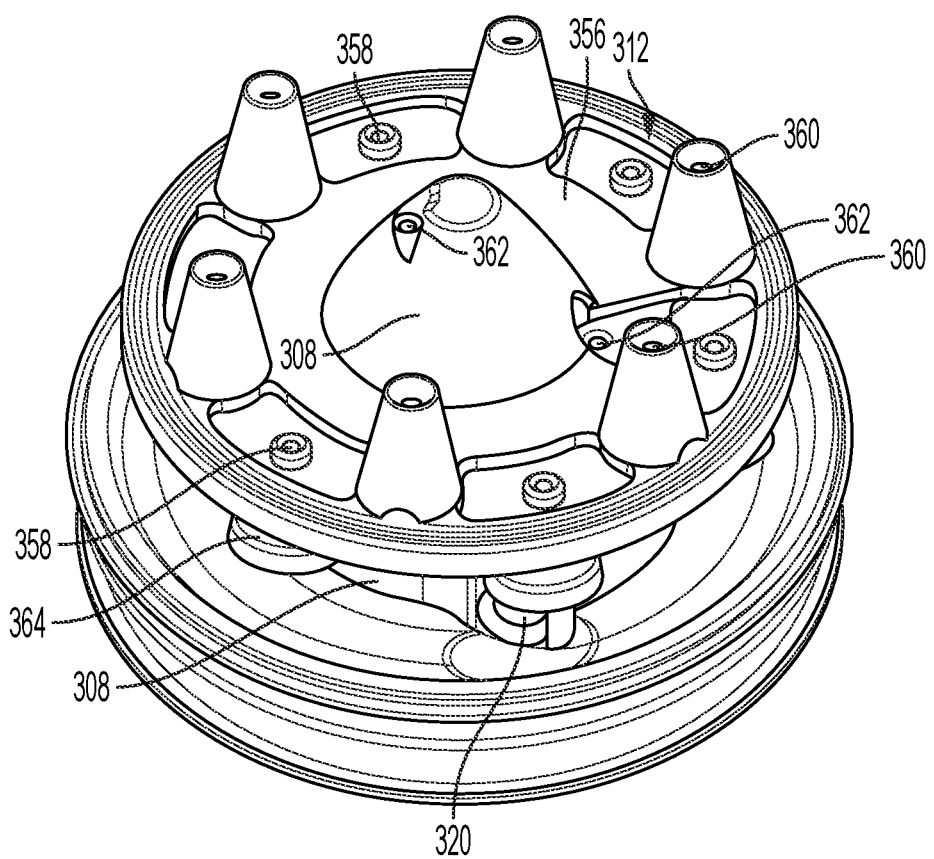
FIG. 3E is a perspective view of a portion of the inlet assembly depicted in FIGS. 3A-3D, in accordance with embodiments of the subject matter disclosed herein.

FIG. 3A is a perspective view of an illustrative respirable inlet assembly 300, in accordance with embodiments of the subject matter disclosed herein; FIG. 3B is a side view of the illustrative respirable inlet assembly 300 depicted in FIG. 3A, in accordance with embodiments of the subject matter disclosed herein; FIGS. 3C and 3D are cross-sectional perspective views of the illustrative respirable inlet assembly 300 depicted in FIGS. 3A and 3B, in accordance with embodiments of the subject matter disclosed herein; and FIG. 3E is a perspective view of a portion of the inlet assembly 300 depicted in FIGS. 3A-3D, in accordance with embodiments of the subject matter disclosed herein. According to embodiments, the respirable inlet assembly 300 may be configured to be received by a receiver of a sampler (e.g., the receiver 110 of the sampler 100 depicted in FIG. 1) to configure the sampler for respirable mass sampling. In embodiments, the respirable inlet assembly 300 may be, be similar to, include, or be included in the respirable inlet assembly 200 depicted in FIGS. 2A and 2B.

As depicted in FIGS. 3A-3E, the respirable inlet assembly 300 includes a hybrid cyclone assembly 302 and a filter cartridge 304. The cyclone assembly 302 includes an upper housing portion 306 within which is disposed a cyclone body 308 having an at least partially conical cyclone cavity 310 defined therein. As shown, the cyclone body 308 may be integrated into a hybrid inlet component 312. A lower housing portion 314 may be configured to be coupled to the upper housing portion 306 to form the cyclone cavity 310. The cavity 310 extends from a cyclone floor 316 of the lower housing portion 314 toward an upper inside surface 318 of the cyclone body 308. As shown in FIGS. 3C, 3D, and 3E, a cyclone inlet aperture 320 is defined through the cyclone body 308, exiting tangentially to the inside surface 322 of the cyclone cavity 310 to impart a rotational characteristic to airflow entering the cavity 310. A size-selective cyclone outlet 324 is defined through the cyclone floor 316.

The filter cartridge 304 includes a filter cartridge housing 326 configured to house a sampling filter 328. The filter cartridge housing 326 includes a filter cartridge base 330 configured to receive the sampling filter 328, and a filter cartridge cap 332 configured to be detachably coupled to the filter cartridge base 330. As shown, the cyclone floor 316 may be coupled to at least a portion of the upper surface of the filter cartridge cap 332. In embodiments, the cyclone floor 316 may be integrated with at least a portion of the upper surface of the filter cartridge cap 332. The size-selective cyclone outlet 324 opens into a sampling chamber 334 defined between an upper surface 336 of the filter cartridge base 330 and a lower surface 338 of the filter cartridge cap 332. The sampling filter 328 may be configured to be disposed within the sampling chamber 334.

As shown, the upper housing portion 306 of the respirable inlet assembly 300 includes an upper wall 340 and a skirt 342 extending downward from the upper wall 340 and disposed around the hybrid inlet component 312 and the lower housing portion 314. The outside surface 344 of the skirt 342 includes a coupling interface 346 configured to removably mate with a corresponding coupling interface of a sampling device receiver (e.g., receiver 110 depicted in FIG. 1). As shown, for example, the coupling interface 346 may be configured to mate with an inner surface of the sampling assembly receiver such as, for example, by coupling corresponding threads together.

When the respirable inlet assembly 300 is assembled, at least a portion of a lower surface 348 of the upper wall 340 and at least a portion of an inner surface 350 of the skirt 342 at least partially define a prequalification chamber 352. A number of primary inlet apertures 354 are defined through the upper wall 340 of the upper housing portion 306, and air flowing into the sampling device first enters into the prequalification chamber 352 through the primary inlet apertures 354. The prequalification chamber 352 is bounded by the portion of the inner surface 350 of the skirt 342, the lower surface 348 of the upper wall 340 of the upper housing portion 306, and an upper surface 356 of the hybrid inlet component 312. In the prequalification chamber 352, the flow slows and very large particles (e.g., particles having a diameter of >>10 μm) may statistically settle on any surface and are lost from subsequent flow. Particles having diameters nearer to 10 μm and below will not settle out of the flow, and are available to be entrained in the subsequent flow.

As shown in FIG. 3E, for example, the hybrid inlet component 312 includes a number of impactor ports 358 defined through the upper surface 356 of the hybrid inlet component 312, impactor bypass ports 360 defined through the upper surface 356 of the hybrid inlet component 312, and a number of cyclone bleed ports 362 defined through the upper surface 356 of the hybrid inlet component 312. Air leaving the prequalification chamber 352 is pulled into any of the impactor ports 358, the impactor bypass ports 360, and the cyclone bleed ports 362, depending on proximity to these ports and the different flow rates each port possesses relative to adjacent ports (which may impact the flow field in the prequalification chamber 352). Embodiments may include any number of ports of the various kinds. In embodiments, the upper housing portion 306 may be configured to be detachably coupled to the hybrid inlet component 312, the lower housing portion 314, and/or filter cartridge 304 via any number of different coupling techniques. As shown, for example, various components may be configured to be detachably coupled to various other components facilitated by any number of different o-rings 364. In embodiments, other coupling techniques may be used.

Air passing through the impactor ports 358 is impacted against impactor target plates 364 for an impaction stage. From the impaction stage, this air enters a secondary chamber 366 defined between a lower surface 368 of the hybrid inlet component 312 and an upper surface 370 of a secondary chamber floor 372, and between an inner surface 350 of the skirt 342 and an outer surface 374 of the lower housing portion 314. Other sample air bypasses the impaction stage and enters the secondary chamber 366 through the impactor bypass ports 360. For example, air jets from these bypass ports 360 may travel about 30 jet diameters before they reach a chamber surface, minimizing impaction. The combined sample flow leaves the secondary chamber 366 by way of a tangential cyclone inlet 320, then goes through the cyclone cavity 310 and exits through the size-selective outlet 324 into the sampling chamber 334.

Additionally, cyclone bleed ports 362 may allow a portion of the sample flow to bypass at least a part of prequalification chamber 352 and secondary chamber 366. In examples, cyclone bleed ports 362 are skewed asymmetrically and/or positioned at different locations of cyclone body 308. As a result, particles passing through cyclone bleed ports 362 may enter cyclone cavity 310 at different portions of the cyclone. Thus, particles entrained in flows entering cyclone cavity 310 may have less chance of being cyclonically separated from the flow as a result of entering the cyclone further downstream as compared to the sample flow entering cyclone cavity 310 via cyclone inlet aperture 320.

The illustrative respirable inlet assembly 300 shown in FIGS. 3A-3E is not intended to suggest any limitation as to the scope of use or functionality of embodiments of the subject matter disclosed throughout this document. The illustrative respirable inlet assembly 300 also should not be interpreted as having any dependency or requirement related to any single component or combination of components illustrated therein. For example, in embodiments, the illustrative respirable inlet assembly 300 can include additional components. Additionally, any one or more of the components depicted in FIGS. 3A-3E can be, in embodiments, integrated with various ones of the other components depicted therein (and/or components not illustrated). Any number of other components or combinations of components can be integrated with the illustrative respirable inlet assembly 300 depicted in FIGS. 3A-3E, all of which are considered to be within the ambit of this disclosure.

Thoracic Mass Inlet

Figure 4A:
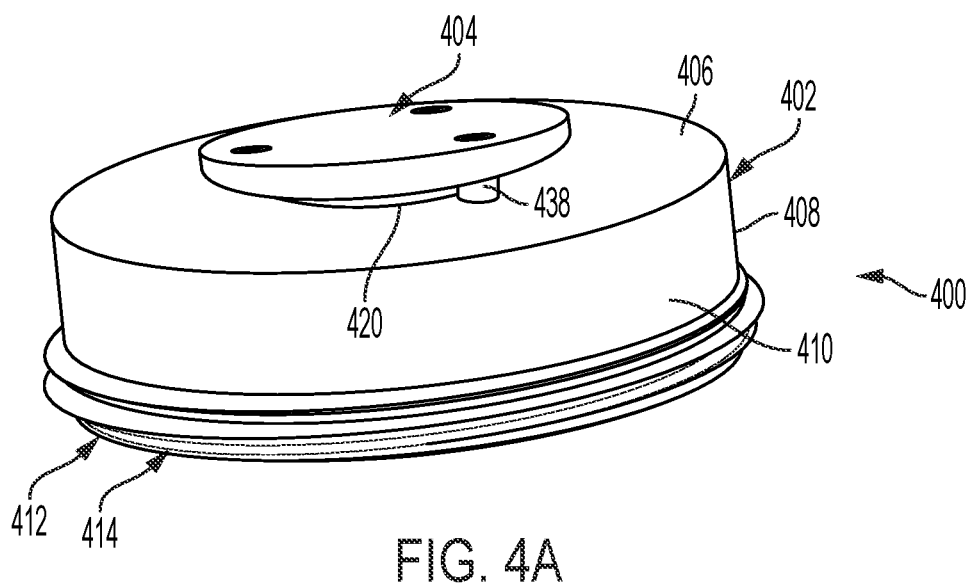
FIG. 4A is a perspective view of an illustrative thoracic inlet assembly, in accordance with embodiments of the subject matter disclosed herein.
Figure 4B:
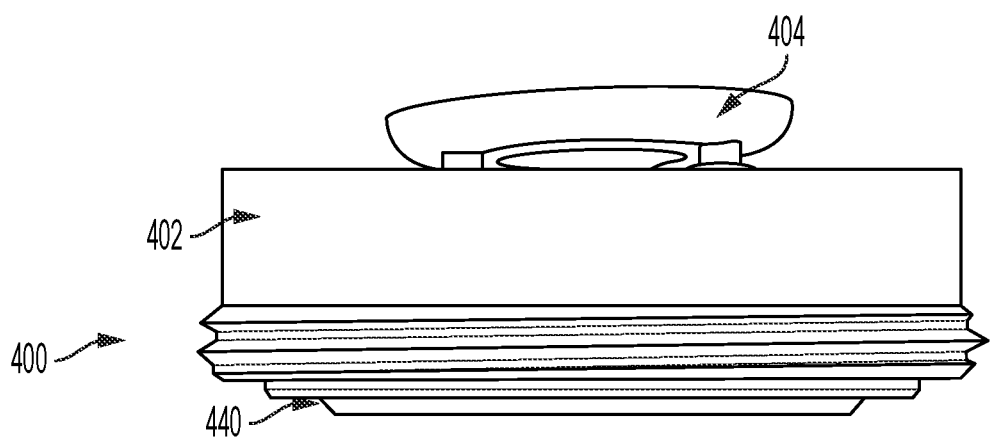
FIG. 4B is a side view of the illustrative thoracic inlet assembly depicted in FIG. 4A, in accordance with embodiments of the subject matter disclosed herein.

FIG. 4A is a perspective view of an illustrative thoracic inlet assembly 400, in accordance with embodiments of the subject matter disclosed herein; and FIG. 4B is a side view of the illustrative thoracic inlet assembly 400 depicted in FIG. 4A, in accordance with embodiments of the subject matter disclosed herein. According to embodiments, the thoracic assembly 400 may be configured to be received by a receiver of a sampler (e.g., the receiver 110 of the sampler 100 depicted in FIG. 1) to configure the sampler for thoracic mass sampling.

As shown in FIGS. 4A and 4B, the thoracic inlet assembly 400 includes an inlet assembly body 402 and a flow limiter 404 disposed on an upper surface 406 of a housing 408 of the assembly body 402. The housing 408 includes a side wall 410 extending down from the upper surface 406. As shown, a thread feature 412 is disposed at the lower end 414 of the housing 408. As shown in FIG. 4A, an inlet aperture 420 is defined in the upper surface 406 of the housing 408. According to embodiments, the flow limiter 404 may be configured to interact with the aperture 420 to form an inlet slot configured to function as a size-selective inlet.

Figure 4C:
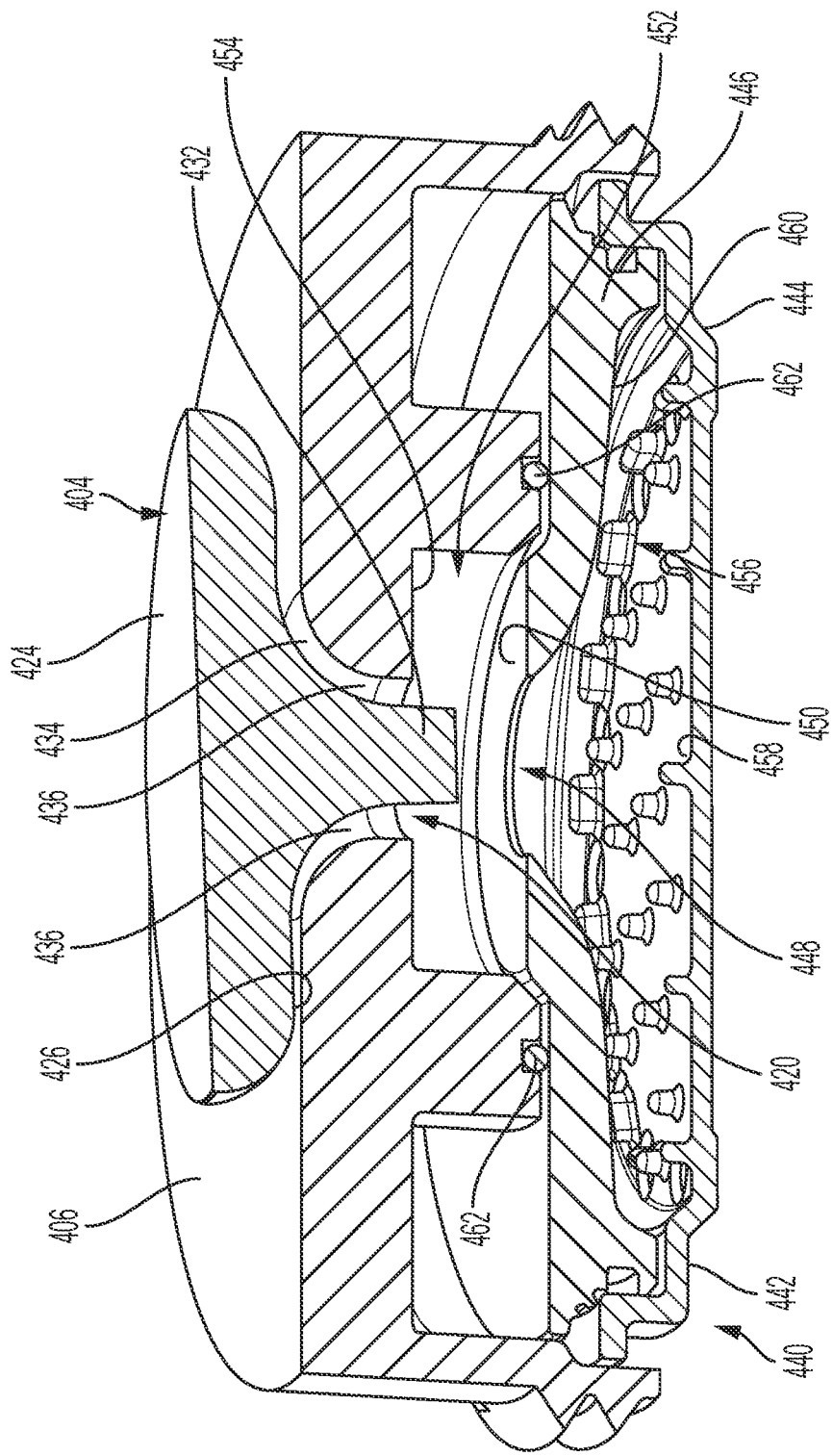
FIG. 4C is a cross-sectional perspective view of the inlet assembly depicted in FIGS. 4A and 4B, in accordance with embodiments of the subject matter disclosed herein.
Figure 4D:
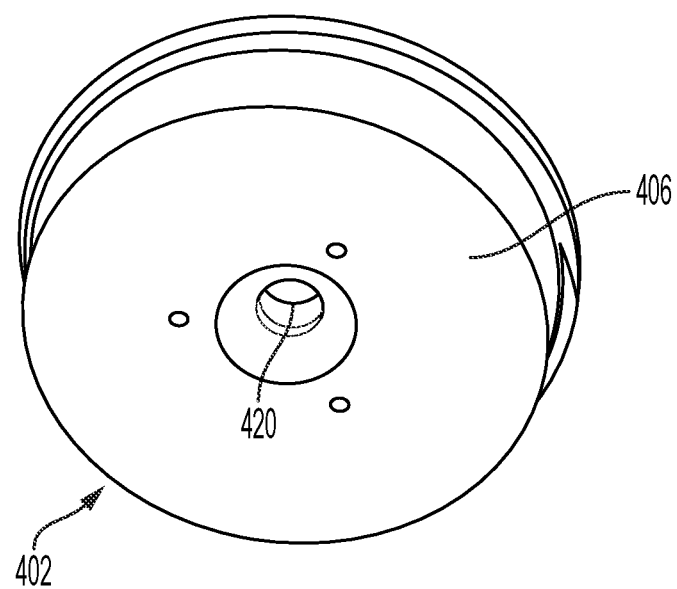
FIG. 4D is an upper perspective view of the inlet assembly body of the inlet assembly depicted in FIGS. 4A-4C, in accordance with embodiments of the subject matter disclosed herein.
Figure 4E:
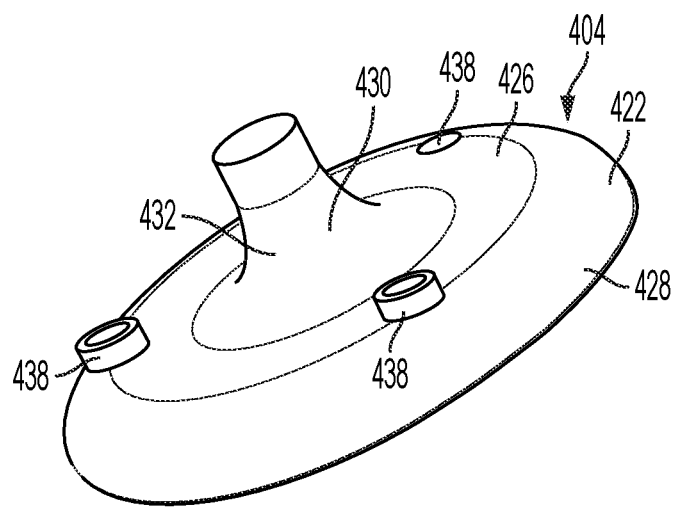
FIG. 4E is a lower perspective view of the flow limiter of the inlet assembly depicted in FIGS. 4A-4C, in accordance with embodiments of the subject matter disclosed herein.

FIG. 4C is a cross-sectional perspective view of the inlet assembly 400 depicted in FIGS. 4A and 4B, in accordance with embodiments of the subject matter disclosed herein;

FIG. 4D is an upper perspective view of the inlet assembly body 402 of the inlet assembly depicted in FIGS. 4A-4C, in accordance with embodiments of the subject matter disclosed herein; and FIG. 4E is a lower perspective view of the flow limiter 404 of the inlet assembly 400 depicted in FIGS. 4A-4C, in accordance with embodiments of the subject matter disclosed herein.

As shown in FIGS. 4C and 4E, the flow limiter 404 includes a dish portion 422 having an upper surface 424 and a lower surface 426. As shown, a side surface 428 may extend between the upper surface 424 and the lower surface 426. In embodiments, the side surface 428 may be integrated with the lower surface 426 and the combination may be referred to, for example, as a curved lower surface 426. The flow limiter 404 may further include a protrusion 430 extending downward from the lower surface 426. As shown, for example, the protrusion 430 may include an outer surface 432 that is at least partially curved and may include, for example, an at least partially conical shape.

As shown in FIG. 4C, at least a portion of the protrusion 430 is configured to be disposed within the aperture 420, thereby at least partially obstructing the aperture so as to create an inlet slot 434 defined, in part, between the upper surface 406 of the housing 408 of the assembly body 402 and the lower surface 426 of the flow limiter 404, and, in part, between a boundary surface 436 of the aperture 420 and the outer surface 432 of the protrusion 430. In embodiments, the boundary surface 436 may be integrated with the upper surface 406 of the housing 408 of the assembly body 402. According to embodiments, the width of the inlet slot 434 at any particular location may be defined by position of the flow limiter 404 and may be configured to prevent particles larger than the width from entering the inlet assembly 404 (and thus, the sampler to which it is coupled). In embodiments, the width of the inlet slot 434 may be constant around the flow limiter 404, while, in other embodiments, the width of the inlet slot 434 may vary around the perimeter of the flow limiter 404. A number of shims 438 may be used to configure the width(s) of the inlet slot 434.

According to embodiments, sampling for thoracic mass requires a fractional collection efficiency of 0.5 for particles about 10 μm in diameter that approaches unity for particles twice that size. In embodiments, the inlet slot 434 may include a simple slot with a 90-degree bend, though the bend radius may be any number of different sizes. The inlet slot 434 may be circular to reduce sensitivity to inlet orientation. The slot length and width may be selected to facilitate a given flow rate. Collection efficiency for particles collected in a slot can be modeled by analogy to collection in a half-jet impactor as $$E = \frac{d^2 v}{18\eta W} \quad (4)$$

where v is gas velocity in the slot, η is gas viscosity, and W is slot width. In embodiments, the slot length and width may be varied to achieve desired collection efficiencies.

As is further shown in FIG. 4C, the inlet assembly 400 may further include a filter cartridge 440. The filter cartridge 440 may include a filter cartridge housing 442 configured to house a sampling filter (not shown) therein. The filter cartridge housing 442 includes a filter cartridge base 444 configured to receive the sampling filter, and a filter cartridge cap 446 configured to be detachably coupled to the filter cartridge base 444. A size-selective outlet 448 may be disposed in an upper surface 450 of the filter cartridge cap 446. As shown, the assembly body 402 includes a cavity 452 defined therein. The cavity 452 extends between a lower surface 454 of the housing 408 and the upper surface 450 of the filter cartridge cap 446. As shown, the size-selective outlet 448 opens into a sampling chamber 456 between an upper surface 458 of the filter cartridge base 444 and a lower surface 460 of the filter cartridge cap 446. The sampling filter may be disposed within the sampling chamber 456. Additionally, in embodiments, as shown in FIG. 4C, an airflow through the inlet assembly 400 may be facilitated, in part, by sealing the filter cartridge cap 446 to the filter cartridge base 444 using a first o-ring (not shown). Similarly, to further facilitate achieving the airflow, the housing 408 may be sealed to the filter cartridge 440 using a second o-ring 462.

The illustrative thoracic inlet assembly 400 shown in FIGS. 4A-4E is not intended to suggest any limitation as to the scope of use or functionality of embodiments of the subject matter disclosed throughout this document. The illustrative thoracic inlet assembly 400 also should not be interpreted as having any dependency or requirement related to any single component or combination of components illustrated therein. For example, in embodiments, the illustrative thoracic inlet assembly 400 can include additional components. Additionally, any one or more of the components depicted in FIGS. 4A-4E can be, in embodiments, integrated with various ones of the other components depicted therein (and/or components not illustrated). Any number of other components or combinations of components can be integrated with the illustrative thoracic inlet assembly 400 depicted in FIGS. 4A-4E, all of which are considered to be within the ambit of this disclosure.

Figure 5A:
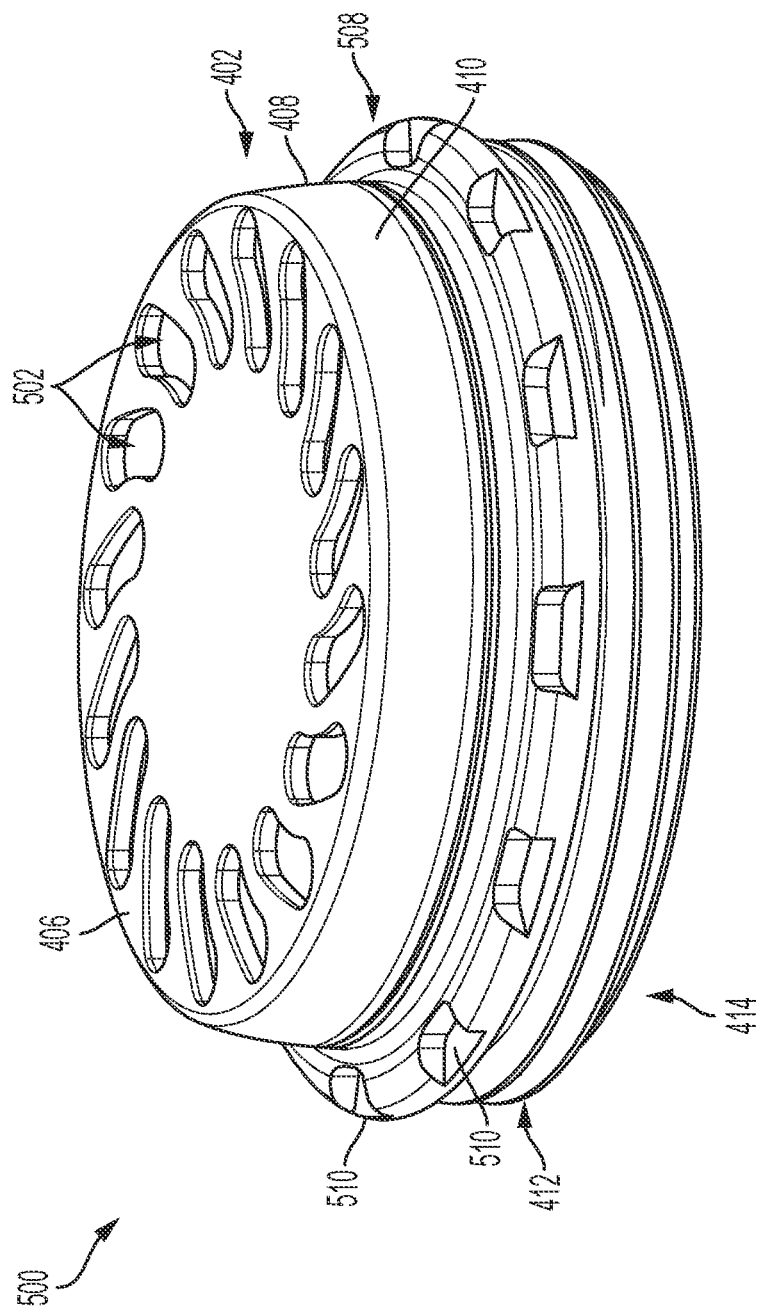
FIG. 5A is a perspective view of an illustrative thoracic inlet assembly, in accordance with embodiments of the subject matter disclosed herein.
Figure 5B:
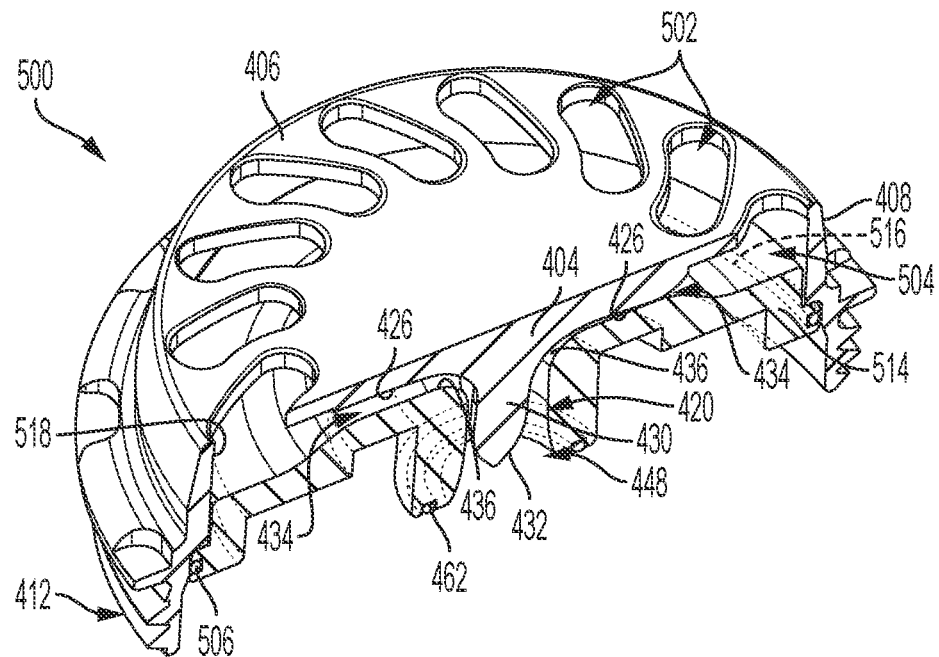
FIGS. 5B and 5C are cross-sectional perspective views of the illustrative thoracic inlet assembly depicted in FIG. 5A, in accordance with embodiments of the subject matter disclosed herein.
Figure 5C:
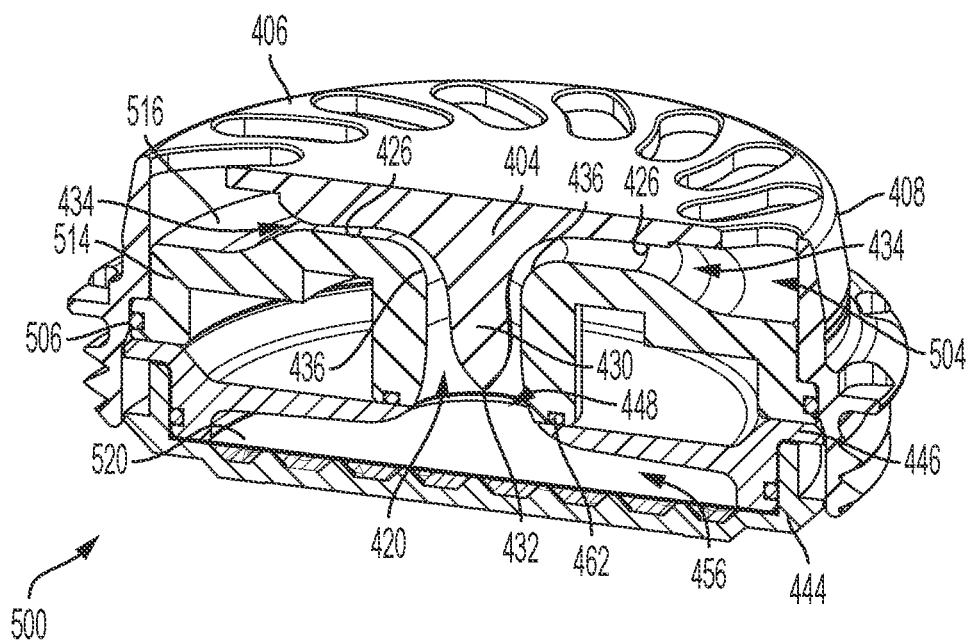
Figure 5D:
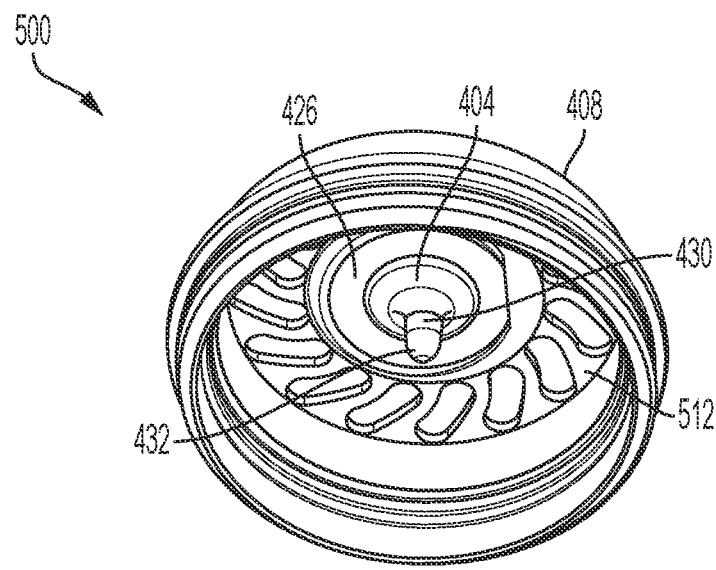
FIGS. 5D and 5E are lower perspective views of the inlet assembly body of the thoracic inlet assembly depicted in FIGS. 5A-5C, in accordance with embodiments of the subject matter disclosed herein.
Figure 5E:
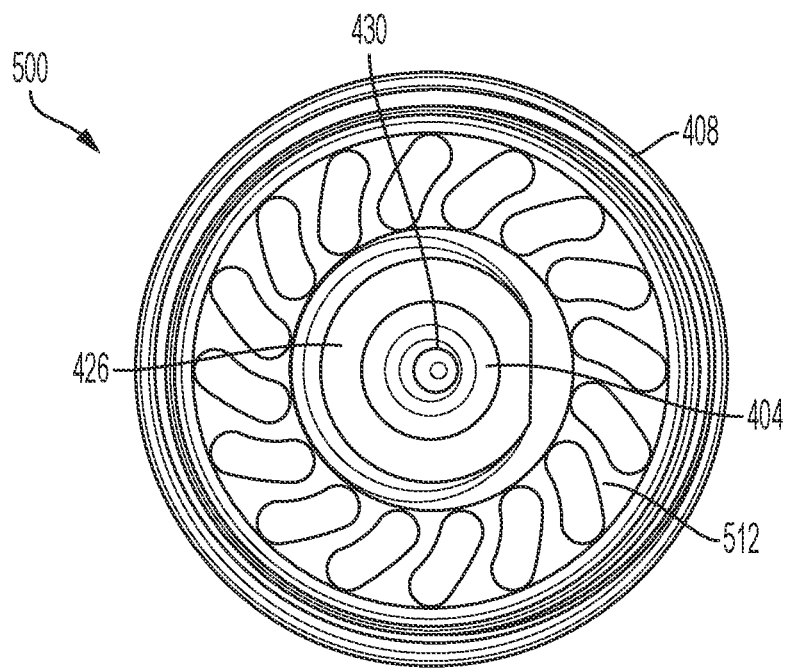

FIG. 5A is a perspective view of an illustrative thoracic inlet assembly 500, in accordance with embodiments of the subject matter disclosed herein; FIGS. 5B and 5C are cross-sectional perspective views of the illustrative thoracic inlet assembly depicted in FIG. 5A, in accordance with embodiments of the subject matter disclosed herein; and FIGS. 5D and 5E are lower perspective views of the inlet assembly body of the thoracic inlet assembly depicted in FIGS. 5A-5C, in accordance with embodiments of the subject matter disclosed herein. According to embodiments, the thoracic inlet assembly 500 may be configured to be received by a receiver of a sampler (e.g., the receiver 110 of the sampler 100 depicted in FIG. 1) to configure the sampler for thoracic mass sampling. In embodiments, the thoracic inlet assembly 500 may be, be similar to, include, or be included in the thoracic inlet assembly 400 depicted in FIGS. 4A-4E.

For example, thoracic inlet assembly 500 incorporates aspects similar to those discussed above with respect to thoracic inlet assembly 400 of FIGS. 4A-4E. Accordingly, such similar aspects are indicated using the same reference numerals as were used with respect to thoracic inlet assembly 400 and are not necessarily re-described below in detail.

Thoracic inlet assembly 500 comprises functional geometry for thoracic particle sampling as described previously. Further, thoracic inlet assembly 500 is designed to facilitate ease of installation or removal into a sampler (e.g., sampler 100 depicted in FIG. 1). Thoracic inlet assembly 500 may be placed upstream of a sampling filter (not pictured). As illustrated, thoracic inlet assembly 500 comprises a thread feature 412 that is disposed at the lower end 414 of the housing 408. Multiple components assemble together to form thoracic inlet assembly 500, which is designed to be retained by a sampler as a whole to achieve practical handling and assembly by the user.

As illustrated, assembly body 402 of thoracic inlet assembly 500 is comprised of a generally cylindrical housing 408. Housing 408 includes an upper surface 406 with a plurality of openings 502 through which sampled air to flows. Each opening 502 is illustrated as having a substantially obround shape that is curved about upper surface 406, thereby increasing the surface area through which the sample airflow can pass (e.g., as compared to a straight obround shape). Housing 408 further includes lower end 414 through which air flows after size selection as described herein. The thread feature 412 is formed onto the outer diameter beginning from the lower end 414 and ending at an overhanging flange 508.

On the opposite side of overhanging flange 508 from the interior end of the thread feature 412 is formed a number of machined pockets 510, which serve as a drive interface for an assembly spanner tool (not shown) at which to apply installation/removal torque. Assembly body 402 has an axial length or height that provides an interior volume that facilitates the aerodynamic function described herein.

FIGS. 5B and 5C illustrate an inlet insert 514 that installs into the lower end 414 of the housing 408 for assembly. In examples, inlet insert 514 is similar to cartridge cap 446. As illustrated, the inlet insert 514 is an axisymmetric part that, when inserted into housing 408, defines the bottom surface 516 of a particle prequalification chamber 504. The inlet insert 514 also contains and defines the boundary surfaces 436 of an aperture 420. The inlet insert 514 may be installed or otherwise inserted into the housing 408. A seal component 506 (typically o-rings) may provide a pneumatic seal between the housing 408 and the inlet insert 514.

When the inlet insert 514 is installed into the housing 408, the protrusion 430 of the flow limiter 404 extends into the aperture 420 in the inlet insert 514. The position and thus relative distances and clearances between these components forms inlet slot 434, which is defined by the geometry of these two parts and the contact surface pairs where the inlet insert 514 and the housing 408 meet. Thus, when the inlet insert 514 is inserted into the housing 408, the critical proximity of all surfaces of the flow limiter 404 (e.g., curved lower surface 426 and outer surface 432) is set relative to the opposite surfaces of the aperture 420 (e.g., boundary surface 436), thus providing the disclosed aerodynamic and particle separation functions. Such aspects may be used as an alternative to the shims 438 discussed herein with respect to other embodiments.

As shown in FIGS. 5D and 5E, flow limiter 404 protrudes from the inner face 512 of the housing 408, which was previously described with respect to FIGS. 4A-4E. The position of flow limiter 404 of thoracic inlet assembly 500 is thus defined by its form from the inner face 512. Openings 502 are arranged around the flow limiter 404, which serve to allow sampled airflow into the overall device. Openings 502 also serve to prevent relatively large airborne and non-airborne objects from entering thoracic inlet assembly 500. For example, the size and shape of openings 502 may prevent very large particles such as large fibers or animal hairs from entering the housing 408.

Thus when the above set of components is assembled, sample airflow is induced into the openings 502 of the upper surface 406 of the housing 408, but relatively large entrained particulates (large fibers or animal hair, for example) are prevented from passing through the openings 502. The sample airflow may then travel axially through the openings 502 and enter the prequalification chamber 504. This prequalification chamber 504 has geometry that facilitates an airflow velocity profile and resident time favorable for additional relatively large particles to separate out of the sample airflow due to either inertial or gravitational effects. For example, such particles may come into contact with and become attached to an interior wall 518 of the housing 408. The sample airflow (and any still-airborne particles therein) may then travel radially inward through the inlet slot 434 toward the flow limiter 404. The sample airflow may turn axially into the annulus between the curved lower surface 426 of the flow limiter 404 and the boundary surfaces 436 of the aperture 420. In this process, particles with diameters and masses larger than those desired for sampling are lost through inertial impaction to the adjacent surfaces, according to the aspects described herein. The sample airflow then passes through a size-selective outlet 448, were it may arrive into a sampling chamber 456, which is defined an upper surface of the filter cartridge base 444 and a lower surface of the filter cartridge cap 446. A sampling filter 520 may be disposed within the sampling chamber 456.

The illustrative thoracic inlet assembly 500 shown in FIGS. 5A-5E is not intended to suggest any limitation as to the scope of use or functionality of embodiments of the subject matter disclosed throughout this document. The illustrative thoracic inlet assembly 500 also should not be interpreted as having any dependency or requirement related to any single component or combination of components illustrated therein. For example, in embodiments, the illustrative thoracic inlet assembly 500 can include additional components. Additionally, any one or more of the components depicted in FIGS. 5A-5E can be, in embodiments, integrated with various ones of the other components depicted therein (and/or components not illustrated). Any number of other components or combinations of components can be integrated with the illustrative thoracic inlet assembly 500 depicted in FIGS. 5A-5E, all of which are considered to be within the ambit of this disclosure.

While the subject matter of embodiments of the disclosure is described with specificity, the description itself is not intended to limit the scope of this patent. Rather, the inventors have contemplated that the claimed subject matter might also be embodied in other ways, to include different steps or features, or combinations of steps or features similar to the ones described in this document, in conjunction with other technologies.

The following is claimed:

1. A respirable inlet assembly for a portable sampling device, comprising:
    an upper housing and a lower housing;
    a number of primary inlet apertures disposed in the upper housing configured to receive a sample airflow; and
    a hybrid cyclone assembly comprising:
        an impaction stage and a cyclone stage in series, wherein the impaction stage and the cyclone stage are arranged so that only a first part of the sample airflow passes through the impaction stage and all of the sample airflow passes through the cyclone stage;
        a number of impactor inlet apertures configured to receive the first part of the sample airflow into the impaction stage from the number of primary inlet apertures; and
        a number of impactor bypass apertures configured to receive a second part of the sample airflow; and
        a number of cyclone bleed ports configured to receive a third part of the sample airflow into the cyclone stage from the number of primary inlet apertures, thereby bypassing the impaction stage.

2. The respirable inlet assembly of claim 1, wherein the number of impactor bypass apertures is configured to reduce an effect of the impaction stage for the second part of the sample airflow as compared to the first part of the sample airflow entering the impaction stage via the number of impactor inlet apertures.

3. The respirable inlet assembly of claim 1, further comprising:
    a number of cyclone bleed ports configured to receive a third part of the sample airflow into the cyclone stage from the number of primary inlet apertures, thereby bypassing the impaction stage.

4. The respirable inlet assembly of claim 1, further comprising:
    a size-selective cyclone outlet defined in the lower housing configured to receive the sample airflow from the cyclone stage into a sampling chamber of the respirable inlet assembly.

5. A portable sampler comprising:
    a sampler assembly having a housing that includes a receiver defined therein for interchangeably receiving a plurality of removable inlet assemblies, and wherein the plurality of removable inlet assemblies includes a respirable inlet assembly, the respirable inlet assembly comprising:

a number of primary inlet apertures disposed in an upper housing configured to receive a sample airflow; and a hybrid cyclone assembly comprising:

an impaction stage and a cyclone stage in series, wherein the impaction stage and the cyclone stage are arranged so that only a first part of the sample airflow passes through the impaction stage and all of the sample airflow passes through the cyclone stage;

a number of impactor inlet apertures configured to receive the first part of the sample airflow into the impaction stage from the number of primary inlet apertures; and a number of impactor bypass apertures configured to receive a second part of the sample airflow; and a number of cyclone bleed ports configured to receive a third part of the sample airflow into the cyclone stage from the number of primary inlet apertures, thereby bypassing the impaction stage.

6. The portable sampler of claim 5, wherein the plurality of removable inlet assemblies further comprises a thoracic inlet assembly, the thoracic inlet assembly comprising:

an assembly housing with an upper surface;

an inlet aperture defined through the upper surface of the assembly housing; and an inlet slot configured to function as a size-selective inlet for the inlet aperture.

7. The portable sampler of claim 6, the thoracic inlet assembly further comprising:

a flow limiter disposed on the upper surface and configured to interact with the inlet aperture to form the inlet slot.

8. The portable sampler of claim 7, wherein the flow limiter comprises:

a dish portion having an upper surface, a lower surface, and a protrusion extending downward from the lower surface, wherein the protrusion is configured to be disposed at least partially within the inlet aperture, thereby at least partially obstructing the inlet aperture so as to create the inlet slot.

9. The portable sampler of claim 8, further comprising one or more shims disposed between the lower surface of the dish portion and the upper surface of the housing, the one or more shims used to configure a width of the inlet slot.

10. The portable sampler of claim 6, wherein the thoracic inlet assembly further comprises a size-selective outlet configured to receive a thoracic sample airflow into a sampling chamber of the thoracic inlet assembly.

11. The respirable inlet assembly of claim 1 wherein the cyclone stage comprises a cyclone inlet configured to receive the first part of the sample airflow and the second part of the sample airflow.

12. The respirable inlet assembly of claim 1, further comprising:

a size-selective cyclone outlet defined in the lower housing configured to receive the sample airflow from the cyclone stage into a sampling chamber of the respirable inlet assembly.

13. The respirable inlet assembly of claim 1 and further comprising one or more impactor target plates configured for the first part of the sample airflow to impact against in the impaction stage.

* * * * *

UNITED STATES PATENT AND TRADEMARK OFFICE
CERTIFICATE OF CORRECTION

PATENT NO. : 12,053,164 B2
APPLICATION NO. : 17/127520
DATED : August 6, 2024
INVENTOR(S) : Leith et al.

Page 1 of 1

It is certified that error appears in the above-identified patent and that said Letters Patent is hereby corrected as shown below:

In the Specification

Column 1, Lines 17-18:
Delete the words "National Institutes of Health", and replace them with --Centers for Disease Control and Prevention--

Signed and Sealed this
First Day of July, 2025

Coke Morgan Stewart
*Acting Director of the United States Patent and Trademark Office*